(12) United States Patent
Zhang et al.

(10) Patent No.: US 10,406,116 B2
(45) Date of Patent: *Sep. 10, 2019

(54) PRESSURE-SENSITIVE ADHESIVES FOR TRANSDERMAL DRUG DELIVERY

(71) Applicant: NOVEN PHARMACEUTICALS, INC., Miami, FL (US)

(72) Inventors: Jilin Zhang, Miami, FL (US); Jun Liao, Miami, FL (US); Puchun Liu, Miami, FL (US); Steven Dinh, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/227,214

(22) Filed: Aug. 3, 2016

(65) Prior Publication Data

US 2016/0374954 A1 Dec. 29, 2016

Related U.S. Application Data

(63) Continuation-in-part of application No. 15/016,698, filed on Feb. 5, 2016.

(60) Provisional application No. 62/112,982, filed on Feb. 6, 2015.

(51) Int. Cl.

| A61K 9/70 | (2006.01) |
|---|---|
| A61K 31/137 | (2006.01) |
| A61K 31/131 | (2006.01) |
| C08F 220/26 | (2006.01) |
| C08F 220/28 | (2006.01) |
| C09J 133/06 | (2006.01) |
| C09J 133/14 | (2006.01) |
| C09J 133/24 | (2006.01) |

(52) U.S. Cl.
CPC .......... *A61K 9/7061* (2013.01); *A61K 9/7084* (2013.01); *A61K 31/131* (2013.01); *A61K 31/137* (2013.01); *C08F 220/26* (2013.01); *C08F 220/28* (2013.01); *C09J 133/06* (2013.01); *C09J 133/14* (2013.01); *C09J 133/24* (2013.01); *C08F 2220/281* (2013.01); *C08F 2220/282* (2013.01); *C08F 2220/285* (2013.01)

(58) Field of Classification Search
None
See application file for complete search history.

(56) References Cited

U.S. PATENT DOCUMENTS

| 4,305,996 A | 12/1981 | Schenk |
| 4,814,168 A | 3/1989 | Sablotsky et al. |
| 4,994,267 A | 2/1991 | Sablotsky et al. |
| 5,234,957 A | 8/1993 | Mantelle et al. |
| 5,300,291 A | 4/1994 | Sablotsky et al. |
| 5,332,576 A | 7/1994 | Mantelle et al. |
| 5,446,070 A | 8/1995 | Mantelle et al. |
| 5,474,783 A | 12/1995 | Miranda et al. |
| 5,646,221 A | 7/1997 | Inagi et al. |
| 5,656,286 A | 8/1997 | Miranda et al. |
| 5,686,099 A | 11/1997 | Sablotsky et al. |
| 5,719,197 A | 2/1998 | Mantelle et al. |
| 5,958,446 A | 9/1999 | Miranda et al. |
| 6,024,974 A | 2/2000 | Li et al. |
| 6,024,976 A | 2/2000 | Miranda et al. |
| 6,221,383 B1 | 4/2001 | Miranda et al. |
| 6,235,306 B1 | 5/2001 | Miranda et al. |
| 6,316,022 B1 | 11/2001 | Mantelle et al. |
| 7,989,496 B2 | 8/2011 | Hartwig et al. |
| 7,993,671 B2 | 8/2011 | Mantelle et al. |
| 8,187,628 B2 | 5/2012 | Houze et al. |
| 8,216,606 B2 | 7/2012 | Houze et al. |
| 8,231,906 B2 | 7/2012 | Mantelle |
| 8,337,884 B2 | 12/2012 | Mantelle et al. |
| 8,343,538 B2 | 1/2013 | Kanios et al. |
| 8,632,802 B2 | 1/2014 | Kanios |
| 8,703,175 B2 | 4/2014 | Kanios et al. |
| 8,715,723 B2 | 5/2014 | Kanios et al. |
| 8,784,877 B2 | 7/2014 | Houze et al. |
| 8,852,628 B1 | 10/2014 | Liao et al. |
| 8,865,207 B2 | 10/2014 | Kanios et al. |
| 8,916,191 B2 | 12/2014 | Kanios |
| 9,034,370 B2 | 5/2015 | Kanios |
| 9,295,726 B2 | 3/2016 | Kulakofsky et al. |
| 9,314,470 B2 | 4/2016 | Patel et al. |

(Continued)

FOREIGN PATENT DOCUMENTS

| WO | WO-2007/100757 A2 | 9/2007 |
| WO | WO 2012/012417 A1 | 1/2012 |

(Continued)

OTHER PUBLICATIONS

Guiseppi-Elie, A., et al., J. Mater. Chem. 22: 19529-19539 (2012).*
International Search Report dated Jun. 13, 2016 in application No. PCT/US2016/016696.
U.S. Appl. No. 60/616,860, filed Oct. 8, 2004, Kanios.
U.S. Appl. No. 60/951,100, filed Jul. 20, 2007, Nguyen.
U.S. Appl. No. 14/974,679, filed Dec. 18, 2015, Kasha et al.
International Search Report dated Oct. 18, 2017 in International Application No. PCT/US2017/044805.

(Continued)

*Primary Examiner* — David J Blanchard
*Assistant Examiner* — Daniel F. Coughlin
(74) *Attorney, Agent, or Firm* — Foley & Lardner LLP

(57) ABSTRACT

Described are pressure-sensitive adhesive polymers (PSAs) useful, for example, for application to the skin, such as in the field of transdermal drug delivery. The PSAs include polar groups modeled on one or more polar portions of skin lipids, which contribute to good skin adhesion properties. Methods of making the PSAs, compositions comprising them, and methods of making and using them also are provided.

17 Claims, 3 Drawing Sheets

(56) References Cited

U.S. PATENT DOCUMENTS

| | | |
|---|---|---|
| 9,320,742 B2 | 4/2016 | Mantelle |
| 2007/0072986 A1 | 3/2007 | Luciano et al. |
| 2007/0238807 A1 | 10/2007 | Safir et al. |
| 2011/0263705 A1 | 10/2011 | Hartwig et al. |
| 2013/0156815 A1 | 6/2013 | Mantelle |
| 2014/0105979 A1 | 4/2014 | Liao et al. |
| 2014/0188056 A1 | 7/2014 | Mori et al. |
| 2014/0200530 A1 | 7/2014 | Mantelle |
| 2014/0243764 A1 | 8/2014 | Kanios et al. |
| 2014/0271792 A1 | 9/2014 | Liao et al. |
| 2014/0271865 A1 | 9/2014 | Lambert et al. |
| 2014/0276478 A1 | 9/2014 | Liao et al. |
| 2014/0276483 A1 | 9/2014 | Liao et al. |
| 2014/0303574 A1* | 10/2014 | Knutson .......... A61F 13/0008 604/307 |
| 2014/0322298 A1 | 10/2014 | Nguyen et al. |
| 2015/0104495 A1 | 4/2015 | Nguyen et al. |
| 2015/0272905 A1 | 10/2015 | Mantelle |
| 2015/0342899 A1 | 12/2015 | Kulakofsky et al. |
| 2016/0015655 A1 | 1/2016 | Mantelle |
| 2016/0030362 A1 | 2/2016 | Liao et al. |
| 2016/0184246 A1 | 6/2016 | Liu et al. |
| 2016/0228383 A1 | 8/2016 | Zhang et al. |
| 2016/0271074 A1 | 9/2016 | Dizio et al. |

FOREIGN PATENT DOCUMENTS

| | | |
|---|---|---|
| WO | WO 2014/159798 A1 | 10/2014 |
| WO | WO-2016/127020 A1 | 8/2016 |

OTHER PUBLICATIONS

Office Action dated Nov. 6, 2017 in U.S. Appl. No. 15/016,698 (US 2016-0228383).

* cited by examiner

Glycosyloxyethyl methacrylate
(GOEMA)

N-[Tris(hydroxymethyl)methyl]acrylamide
(TRIS-OH)

10,406,116 B2

PRESSURE-SENSITIVE ADHESIVES FOR TRANSDERMAL DRUG DELIVERY

CROSS-REFERENCE TO RELATED PATENT APPLICATIONS

This application is a continuation-in-part of U.S. patent application Ser. No. 15/016,698 filed Feb. 5, 2016, which claims the priority benefits under 35 USC § 119(e) to U.S. provisional application 62/112,982, filed Feb. 6, 2015, the entire contents of both of which are incorporated herein by reference in their entireties.

BACKGROUND

The present invention relates generally to pressure-sensitive adhesives useful, for example, for application to the skin, such as in the field of transdermal drug delivery. Methods of making the pressure-sensitive adhesives, compositions comprising them, and methods of making and using them also are provided.

Pressure-sensitive adhesives (PSAs) used for application to the skin are designed to satisfy often competing criteria, including criteria related to desired adhesion properties, cohesion properties, and wear properties, as well as being compatible with skin and non-irritating. PSAs used in transdermal drug delivery systems, such as transdermal patches, also may be designed to satisfy additional criteria, such as compatibility with the drug(s) and other components present in the transdermal drug delivery systems, e.g., such PSAs may be designed to solubilize the drug(s) while exhibiting good drug flux, and not be reactive with the drug(s) and other components.

PSAs suitable for use in transdermal drug delivery systems are known. Nevertheless, there remains a need for PSAs that exhibit strong bonding characteristics.

SUMMARY

In accordance with some embodiments, there are provided transdermal drug delivery compositions comprising an amine drug and a pressure-sensitive adhesive polymer (PSA) polymerized from monomers including skin-mimicking monomers having a skin-mimicking polar group, weakly hydrophilic monomers, and hydrophobic monomers, wherein the skin-mimicking monomer is selected from the group consisting of monomers having a glucosyl group, monomers having two or more hydroxyl groups, and combinations of any two or more thereof. In some embodiments, the PSA has a three-part structure comprising a skin-mimicking portion formed from monomers including skin-mimicking monomers, a weakly hydrophilic portion formed from monomers including hydrophilic monomers, and a hydrophobic portion former from monomers including hydrophobic monomers. In some embodiments, the PSA is polymerized from further monomers selected from the group consisting of hydrophilic hydroxyethyl methacrylate (HEMA), hydroxyethyl acrylate (HEA), acrylic acid (AA), methyl acrylic acid (MAA), and combinations of any two or more thereof. The skin-mimicking monomers may be selected from the group consisting of GOEMA, TRIS-OH, 2,3-dihydroxylpropyl acrylate, glycerol monomethacrylate, 1,1,1-trimethylolpropane monoallyl ether, pentaerythritol mono-acrylate, pentaerythritol mono-methacrylate, sorbitol mono-acrylate, sorbitol mono-methacrylate, and acrylates containing one or more catechol groups, and combinations of any two or more thereof. The weakly hydrophilic monomers may be selected from the group consisting of methoxy ethylacylate (MEA), polyethylene glycol mono-methacrylate (PEGMA), and combinations thereof. The hydrophobic monomers may be selected from the group consisting of vinyl acetate (VA), methyl methacrylate (MMA), methyl acrylate (MA), n-butyl acrylate (n-BA), 2-ethylhexyl acrylate (2-EHA), tris(trimethylsilyloxy)silyl)propyl methacrylate (TRIS-Si), and combinations of any two or more thereof. In specific embodiments, the PSA has a three-part structure comprising a skin-mimicking portion formed from TRIS-OH monomers, a weakly hydrophilic portion formed from MEA monomers, and a hydrophobic portion formed from MA, EHA and TRIS-Si monomers.

In accordance with some embodiments, the amine drug is comprised in a drug-in-adhesive matrix comprising the PSA. In accordance with other embodiments, the PSA is comprised in a non-drug containing layer.

In accordance with some embodiments, the transdermal drug delivery composition

In accordance with some embodiments, the transdermal drug delivery composition exhibits a peel force from the release liner of 20-45 g/0.5" after storage for three or four months at ambient conditions, such as 20-25° C. and 30-70% relative humidity.

In accordance with some embodiments, the amine drug is one or more selected from the group consisting of amphetamine, methylphenidate, rivastigmine, rotigotine, fentanyl, paroxetine clonidine, amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, flavoxate, homatropine, imipramine, loxapine, mazaticol, metixene, oxybutin, oxyphencyclimine, phenglutarimide, physostigmine, piperidolate, pirenzepine, procycli dine, profenamine, propiverine, scopolamine, telenzepine, theophylline, tolterodine, trimipramine, trihexyphenidyl, tropatepine, and tropicamide.

In accordance with other embodiments, there are provided methods of making a transdermal drug delivery composition comprising blending a PSA as described herein with an amine drug, or comprising forming a transdermal drug delivery composition comprising a non-drug containing layer comprising a PSA as described herein and a polymer matrix layer comprising an amine drug.

In accordance with other embodiments, there are provided methods of transdermally delivering an amine active agent, comprising applying a transdermal drug delivery composition as described herein to the skin of a subject in need thereof. In some embodiments, the composition remains adhered to the skin upon exposure to water.

DETAILED DESCRIPTION

Figure 1:
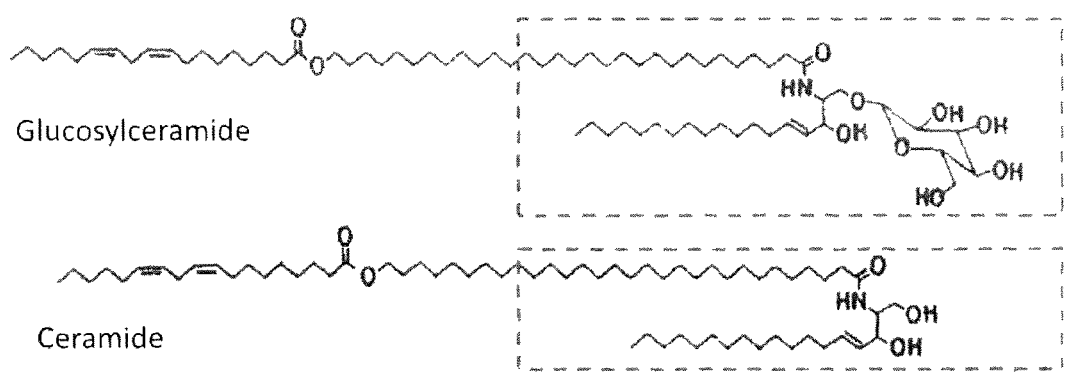
FIG. 1 sets forth the chemical structures of two skin lipids, glucosylceramide and ceramide.

Described herein are PSAs useful, for example, for application to the skin, such as in the field of transdermal drug delivery, bandages, or adhering devices to the skin. The PSAs include polar groups modeled on one or more polar portions of skin lipids, which contribute to good skin adhesion properties. Without being bound by any theory, it is believed that hydrogen bonding occurs between such polar groups on the PSAs and skin lipids, thereby strongly adhering the PSAs to skin.

DEFINITIONS

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein means that the described composition (e.g., polymer matrix, etc.) comprises less than about 5%, less than about 3%, or less than about 1% by weight, based on the total weight of the composition at issue, of the excluded component(s).

As used herein, the terms "topical" and "topically" mean application to a skin or mucosal surface of a mammal, while the terms "transdermal" and "transdermal" connote passage through the skin or mucosa (including oral, buccal, nasal, rectal and vaginal mucosa), into systemic circulation. Thus, as used herein, transdermal compositions may be applied topically to a subject to achieve transdermal delivery of a drug.

As used herein, the term "pressure-sensitive adhesive" refers to a viscoelastic material which adheres instantaneously to most substrates with the application of slight pressure and remains permanently tacky. As noted above, a polymer is a pressure-sensitive adhesive polymer if it has the properties of a pressure-sensitive adhesive per se. Other polymers may function as a pressure-sensitive adhesive by admixture with tackifiers, plasticizers and/or other additives. The term pressure-sensitive adhesive also includes mixtures of different polymers.

Figure 2:
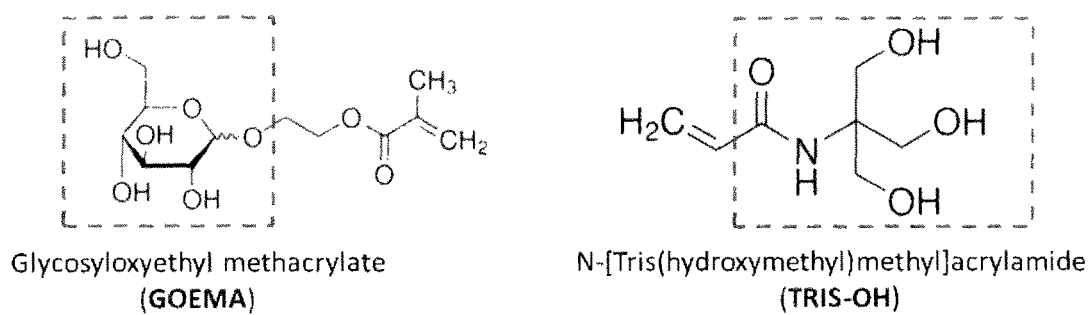
FIG. 2 sets forth the chemical structures of glycosyloxyethyl methacrylate (GOEMA) and N-[Tris(hydroxylmethyl)methyl]acrylamide (TRIS-OH).

As noted above, the PSAs described herein include polar groups modeled on one or more polar portions of skin lipids, which contribute to good skin adhesion properties. The PSAs can be synthesized by copolymerization of appropriate monomers, including monomers that have polar groups that are the same as or similar to polar groups present on skin lipids. (Such polar groups are referred to herein as "skin-mimicking polar groups", while monomers having such polar groups are referred to herein as "skin-mimicking monomers.") This is illustrated with reference to two skin lipids, glucosylceramide and ceramide, the structures of which are set forth in FIG. 1. As shown in FIG. 1, glucosylceramide contains polar glucosyl and hydroxy groups, while ceramide contains a polar bi-(hydroxymethyl) group. Thus, in specific embodiments, the PSAs described herein may include one or more of these polar groups, or polar groups similar to them. For example, the monomer glycosyloxyethyl methacrylate (GOEMA) contains the same glucosyl group as glucosylceramide, and so is useful to make PSAs described herein. Likewise, monomers having an n-(hydroxymethyl) group, wherein n is an integer from 2-6 can be used. The monomer N-[Tris(hydroxylmethyl)methyl] acrylamide (TRIS-OH) contains a tris(hydroxymethyl) group, which is similar to the bi-(hydroxymethyl) group of ceramide, and also is useful to make PSAs described herein. (The chemical structures of GOEMA and TRIS-OH are set forth in FIG. 2.) Other monomers that can be used as skin-mimicking monomers include those containing two or more hydroxyl groups, such as 2,3-dihydroxylpropyl acrylate, glycerol monomethacrylate, 1,1,1-trimethylolpropane monoallyl ether, pentaerythritol mono-acrylate, pentaerythritol mono-methacrylate, sorbitol mono-acrylate, sorbitol mono-methacrylate, acrylates containing one or more catechol groups (such as, for example, 2-(3,4-dihydroxyphenyl)-ethyl acrylate, 2-(3,4-dihydroxyphenyl)-ethyl methacrylate, 2-(3,4-dihydroxyphenyl)-ethyl acrylamide, 2-(3,4-dihydroxyphenyl)-ethyl methacrylamide), and the like.

Figure 3:
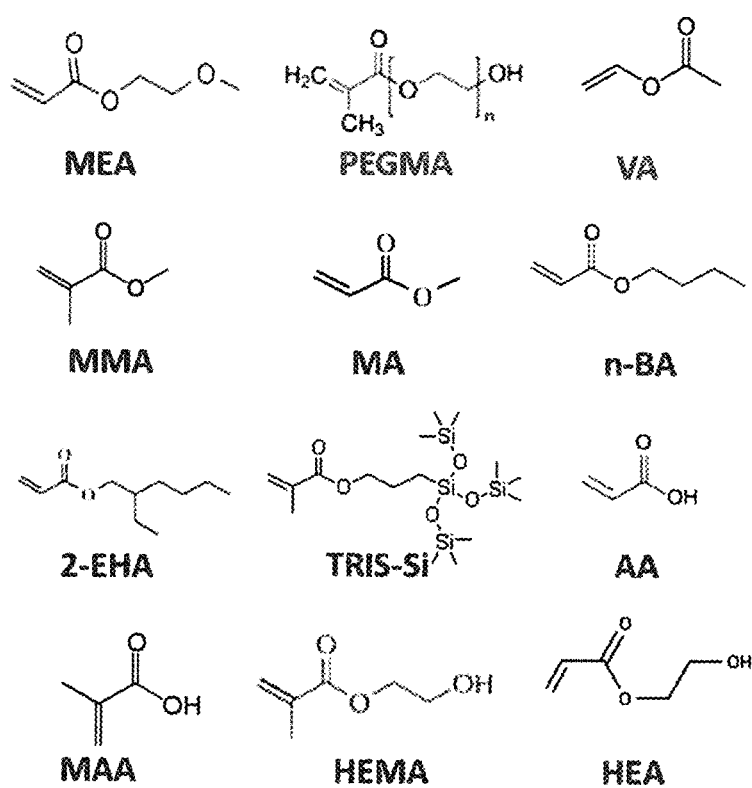
FIG. 3 sets forth the chemical structures of methoxy ethylacylate (MEA), polyethylene glycol monomethacrylate (PEGMA), vinyl acetate (VA), methyl methacrylate (MMA), methyl acrylate (MA), n-butyl acrylate (n-BA), 2-ethylhexyl acrylate (2-EHA), tris(trimethylsilyloxy)silyl) propyl methacrylate (TRIS-Si), acrylic acid (AA), methyl acrylic acid (MAA), hydroxyethyl methacrylate (HEMA), and hydroxyethyl acrylate (HEA).

As noted above the PSAs described herein can be synthesized by copolymerization of suitable monomers, including monomers that have skin-mimicking polar group (such as GOEMA and/or TRIS-OH and others described herein), optionally with other monomers useful to make PSAs, such as acrylic or vinyl monomers useful to make PSAs for transdermal applications. In some embodiments, the PSAs are copolymerized from several different types of monomers, selected to provide desired properties. For example, a first monomer type may be monomers with skin-mimicking polar groups (e.g., GEOMA and/or TRIS-OH). A second monomer type may be weakly hydrophilic monomers (e.g., MEA and/or PEGMA). A third monomer type may be hydrophobic monomers (e.g., VA, MMA, MA, n-BA, 2-EHA, TRIS-Si, etc.). Other types of skin-mimicking monomers could mimic cholesterol or free fatty acids present in the skin, which have sterol groups (e.g., hydroxyl group) and carboxyl groups, respectively. Other monomer types that optionally may be used include hydrophilic monomers containing a single hydroxyl or carboxyl group (e.g., acrylic acid (AA), hydroxyethyl methacrylate (HEMA), and/or hydroxyethyl acrylate (HEA, etc.). Table 1 sets forth examples of acrylic monomers (and the glass transition temperature (Tg) of their homopolymers) that can be used to synthesize the PSAs described herein. The chemical structures of these monomers are set forth in FIG. 3. The adhesion and cohesion properties of the PSAs described herein can be selected and controlled by selecting monomers with appropriate Tg values and varying the ratios of the monomers used to make a given PSA.

TABLE 1

Exemplary monomers and the glass transition temperature ($T_g$) of their homopolymers.

| | Monomers | Tg (° C.) |
|---|---|---|
| Skin Mimicking monomers | Tris(hydroxylmethyl)methyl]acrylamide (TRIS-OH) | 156 |
| | Glycosyloxyethyl methacrylate (GOEMA) | — |
| Weakly hydrophilic monomers | Methoxy ethylacylate (MEA) | −50 |
| | Polyethylene glycol monomethacrylate (PEGMA) | — |
| Optional hydrophilic monomers | Acrylic acid (AA) | 105 |
| | Hydroxyethyl methacrylate (HEMA) | 57 |
| | Hydroxyethyl acrylate (HEA) | −16 |
| Hydrophobic monomer | Methyl acrylate (MA) | 9 |
| | Methyl methacrylate (MMA) | 105 |
| | n-Butyl acrylate (nBA) | −54 |
| | 2-Ethylhexyl acrylate (2-EHA) | −68 |
| | Tris(trimethylsilyloxy)silyl)propyl meth-acrylate (TRIS-Si) | −5 |

In further specific embodiments, the PSAs are designed to have a structure including a skin-mimicking portion, an intermediate hydrophilic portion and a hydrophobic portion. In accordance with such embodiments, the skin-mimicking portion may be formed from monomers that have skin-mimicking polar groups (e.g., polar groups that are the same as or similar to polar groups present on skin lipids, such as GOEMA and/or TRIS-OH), optionally together with other hydrophilic monomers, such as MAA, AA, HEMA and/or HEA; the intermediate hydrophilic portion may be formed from monomers that are weakly hydrophilic, such as monomers that are swellable in but insoluble in water, such as MEA and/or PEGMA, and the hydrophobic portion may be formed from monomers that are hydrophobic, such as VA, MMA, MA, n-BA, 2-EHA, and/or TRIS-Si. For convenience, such PSAs are referred to herein below as PSAs having a "three-part structure" although it is to be understood that such a PSA could include other portions or regions, comprising, for example, other monomers, functional groups or substituents. The polymers described herein can be random copolymers (e.g., with a random arrangement of monomers) or block copolymers (e.g., with an ordered arrangement of monomers, in any order).

Figure 4:
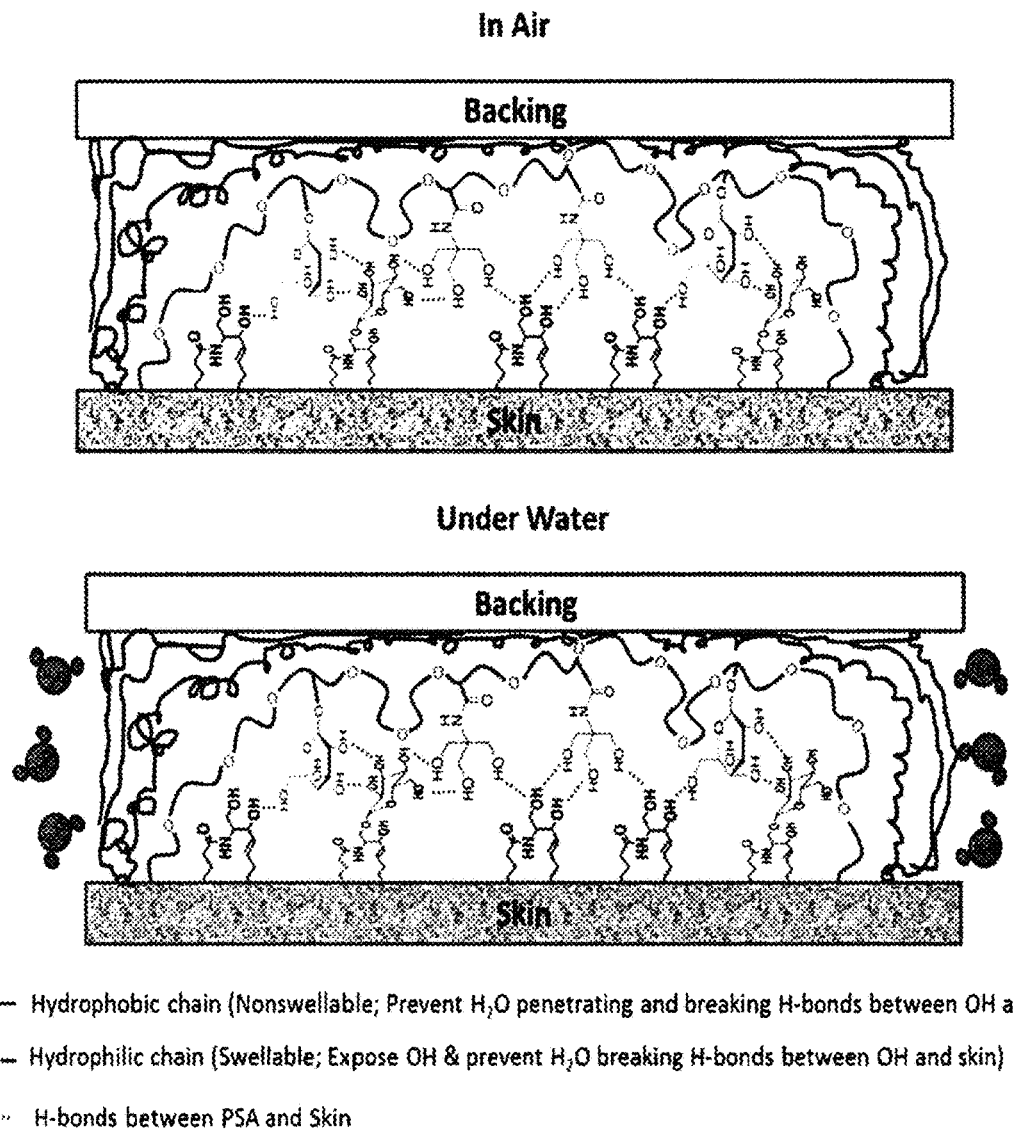
FIG. 4 depicts a possible configuration of a PSA as described herein with a three-part structure in the context of a transdermal patch.

While not wanting to be bound by theory, it is believed that PSAs with a three-part structure as described herein have an advantageous working mechanism upon application to skin. This mechanism is illustrated in FIG. 4 in the context of a transdermal composition comprising a PSA as described herein and a backing, such as a transdermal patch. In accordance with this understanding of the working mechanism, the skin-mimicking portion mainly locates in a region contacting the skin (likely due to its high surface energy), where the hydrogen bond-forming moieties (e.g., the glucosyl hydroxy and bi-(hydroxymethyl) groups) may form strong hydrogen bonds with polar portions of skin lipids, thereby providing good adhesion to skin. (Relevant interaction force strength and working distance properties are set forth in Table 2) The intermediate hydrophilic portion bridges the skin-mimicking portion and the hydrophobic portion, and may surround, protect and/or stabilize the skin-mimicking portion, and may reduce, minimize, or prevent phasing between the skin-mimicking portion and the hydrophobic portion. The hydrophobic portion mainly locates in a region away from the skin (likely due to its low surface energy).

TABLE 2

General interaction force strength and working distance.

| Interaction Force | Strength (kJ/mol) | Distance (nm) |
|---|---|---|
| Van der Waals | 0.4-4.0 | 0.3-0.6 |
| Hydrogen Bonds | 12-30 | 0.3 |
| Ionic Interactions | 20 | 0.25 |
| Hydrophobic Interactions | <40 | varies |

PSAs with a three-part structure as described herein may offer particular advantages with regard to their performance upon exposure to water. Again, while not wanting to be bound by theory, it is believed that when a composition comprising such a PSA (such as a transdermal patch composition) is exposed to water, the hydrophobic portion may reduce, minimize or prevent water from penetrating the composition, or from getting in between the composition and the skin. Further, water molecules that penetrate the hydrophobic portion may be absorbed by the hydrophilic intermediate portion. Thus, the hydrophobic portion and the hydrophilic intermediate portion may reduce, minimize or prevent water from reaching the skin-mimicking portion, such that the skin-mimicking portion may remain dry even if the composition as a whole is exposed to water. By reducing, minimizing or preventing water from reaching the skin-mimicking portion, competition for the hydrogen bonds formed between the skin-mimicking portion and the skin is reduced, minimized or prevented, such that the PSA exhibits good skin adhesion even upon exposure to water, such as ambient moisture. Thus, in some embodiments, the PSAs described herein are "waterproof" or "water-resistant" in that they are capable of securely bonding to the skin and reduce, minimize, or prevent water from penetrating into the composition, even upon exposure to or immersion in water, such as in the context of swimming or bathing.

In some embodiments, the PSAs described herein are pressure-sensitive adhesive at room temperature and exhibit desirable physical properties, such as good adherence to skin, ability to be peeled or otherwise removed without substantial trauma to the skin, retention of tack with aging, etc. In some embodiments, the PSAs have a glass transition temperature (Tg), measured using a differential scanning calorimeter or rheometer, of between about −70° C. and 10° C.

As noted above, the PSAs described herein are useful, for example, for application to the skin, such as in the field of transdermal drug delivery. The PSAs described herein also can be used in other skin contact applications, such as to adhere a bandage or other device to the skin, such as a medical device or wearable personal device.

Transdermal Drug Delivery Compositions

The PSAs described herein can be used in a transdermal composition that is in a "flexible, finite form." As used herein, the phrase "flexible, finite form" means a substantially solid form capable of conforming to a surface with which it comes into contact, and capable of maintaining contact so as to facilitate topical application. In some embodiments, transdermal composition as described herein may comprise a drug-containing polymer matrix that releases one or more drugs upon application to the skin. (As used herein, "drug-containing polymer matrix" refers to a polymer composition which contains one or more drugs, and a polymer, such as a PSA as described herein, or another pressure-sensitive adhesive polymer or bioadhesive polymer.) Such compositions in general are known in the art and commercially available, such as transdermal drug delivery patches. In some embodiments, a transdermal composition in flexible, finite form also includes a backing layer. In some embodiments, a composition in flexible, finite form may also include a release liner layer that is removed prior to use. In some embodiments, a transdermal composition may include one or more other layers, such as one or more skin-adhering, drug-containing and/or rate-controlling layers. Thus, the PSAs described herein may be used in transdermal patches, e.g., as an adhesive component of a drug-in-adhesive matrix or as a non-drug containing adhesive that promotes adhesion of the patch to the skin or performs another function, such as controlling the rate or pharmacokinetic profile of drug delivery.

In some embodiments, the PSAs described herein are used as polymer component(s) of a "monolithic" or "monolayer" transdermal drug delivery composition, e.g., in a drug-containing polymer matrix layer that is the only polymeric layer present other than the backing layer and the release liner, if present. In such embodiments, the polymer matrix functions as both the drug carrier and the means of affixing the composition to the skin. In other embodiments the PSAs described herein serve as an adhesive component of a transdermal drug delivery composition that includes a separate drug-containing layer (e.g., a reservoir-type system), or as an adhesive component of one or more other layers of a multi-layer system. In some embodiments, the PSAs described herein are used in one or more layers of a multi-layer system and/or serve one or more different roles in a transdermal drug delivery composition, such as a skin-adhering or drug delivery-controlling function.

As noted above, the polymer matrix of the compositions described herein optionally may further comprise (in addition to the PSAs described herein, other optional polymer components, and one or more active agents) other components typically used in a transdermal drug delivery composition, such as tackifiers, plasticizers, crosslinking agents or other excipients known in the art.

The transdermal drug delivery compositions may be of any shape or size suitable for transdermal application, such as ranging from 2 cm$^2$ to 80 cm$^2$.

Active Agents

The PSAs described herein can be used in transdermal drug delivery compositions for any active agent, such as any topically or systemically active agent (e.g., any drug), such as any agent useful for the treatment or prevention of any disease or condition, or for health maintenance purposes. In specific embodiments, the active agent is not reactive to hydroxyl groups. That is, in specific embodiments, the active agent does not include functional groups that are reactive to hydroxyl groups. Examples of drugs which may be formulated in the PSAs described herein include without limitation amphetamine, methylphenidate, rivastigmine, paroxetine, clonidine, fentanyl, rotigotine, agomelatine, nicotine, estradiol, ethinyl estradiol, estriol, norelgestromin, levonorgestrel, gestodene, norethindrone, and norethindrone acetate, and combinations of any two or more thereof.

In some embodiments, the active agent is an amine drug, including a primary amine drug, a secondary amine drug and/or a tertiary amine drug. In specific embodiments, the active agent is one or more amine drug selected from the group consisting of amphetamine, methylphenidate, rivastigmine, rotigotine, fentanyl, paroxetine clonidine, amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, flavoxate, homatropine, imipramine, loxapine, mazaticol, metixene, oxybutin, oxyphencyclimine, phenglutarimide, physostigmine, piperidolate, pirenzepine, procyclidine, profenamine, propiverine, scopolamine, telenzepine, theophylline, tolterodine, trimipramine, trihexyphenidyl, tropatepine, and tropicamide.

Transdermal drug delivery compositions comprising one or more active agents can be used to administer the active agent(s) for therapeutic benefit, e.g., to treat the disease or condition for which the active agent is useful for treating. Thus, for example transdermal drug delivery compositions comprising amphetamine may be used, for example, for achieving central nervous system stimulation, for the treatment of Attention Deficit Disorder (ADD) and/or Attention Deficit/Hyperactivity Disorder (ADHD), and/or for the treatment of narcolepsy; transdermal drug delivery compositions comprising methylphenidate may be used, for example, for the treatment of ADD and/or ADHD; transdermal drug delivery compositions comprising rivastigmine may be used, for example, for the treatment of mild to moderate dementia of the Alzheimer's type and dementia due to Parkinson's disease; transdermal drug delivery compositions comprising rotigotine may be used, for example, for the treatment of Parkinson's disease or restless legs syndrome; transdermal drug delivery compositions comprising fentanyl may be used, for example, for the treatment of pain; transdermal drug delivery compositions comprising paroxetine may be used, for example, for the treatment of major depression, obsessive-compulsive disorder, panic disorder, social anxiety, post-traumatic stress disorder, generalized anxiety disorder and vasomotor symptoms (e.g. hot flashes and night sweats) associated with menopause; transdermal drug delivery compositions comprising clonidine may be used, for example, for the treatment of high blood pressure, attention-deficit/hyperactivity disorder, anxiety disorders, withdrawal (from either alcohol, opioids or smoking), migraine, menopausal flushing, diarrhea and certain pain conditions; transdermal drug delivery compositions comprising nicotine may be used, for example, for the treatment of nicotine addiction; transdermal drug delivery compositions comprising one or more of estradiol, ethinyl estradiol, estriol, norelgestromin, levonorgestrel, gestodene, norethindrone, and norethindrone acetate, may be used, for example, in methods of contraception.

Backing Layer

As noted above, compositions in flexible, finite form comprise a polymer matrix, such as described above, and a backing layer. The backing layer is impermeable to the drug and is adjacent one face of the polymer matrix. (By "impermeable" to the drug is meant that no substantial amount of drug loss through the backing layer is observed) The backing layer protects the polymer matrix from the environment and prevents loss of the drug and/or release of other components to the environment during use. Materials suitable for use as backing layers are well-known in the art and commercially available.

Release Liner

As noted above, compositions in flexible, finite form may further comprise a release liner, typically located adjacent the opposite face of the system as the backing layer. When present, the release liner is removed from the system prior to use to expose the polymer matrix layer prior to topical application. Materials suitable for use as release liners are well-known in the art and commercially available.

Methods of Manufacture

The transdermal compositions described herein can be prepared by methods known in the art. For example, a drug-in-adhesive matrix can be prepared by methods known in the art, such as blending (mixing) the polymer component(s) in powder or liquid form with an appropriate amount of drug in the presence of an appropriate solvent, such as a volatile organic solvent, optionally with other excipients. To form a final product, the drug/polymer/solvent mixture may be cast onto a release liner, followed by evaporation of the volatile solvent(s), for example, at room temperature, slightly elevated temperature, or by a heating/drying step, to form the drug-containing polymer matrix on a release liner. A pre-formed backing layer may be applied to form a final product. Appropriate size and shape delivery systems are die-cut from the roll material and then pouched. Similar methods can be used to prepare non-drug containing polymer layers.

The order of steps, the amount of the ingredients, and the amount and time of agitation or mixing may be important process variables which will depend on the specific polymers, active agents, solvents and/or cosolvents, and optional excipients used in the composition, but these factors can be adjusted by those skilled in the art. The order in which each method step is performed can be changed if needed without detracting from the invention.

The following specific examples are included as illustrative of the subject matter described herein. These example are in no way intended to limit the scope of the invention. Other aspects of the invention will be apparent to those skilled in the art to which the invention pertains.

EXAMPLES

Example 1

PSAs 1-12

PSAs as described herein are synthesized by copolymerization of appropriate acrylic monomers (as exemplified in Table 3 below) in butanone/ethanol mixed solvents with AIBN as the initiator at 80° C.

Example 2

PSAs A-C

PSAs A-C (50 g each) were polymerized from the monomers set forth in Table 4 below using the initiator AIBN (M/1=100) in a 250 ml round-bottom flask with 46.4 ml of 2-butanone and ethanol mixed solvent (1:1, v/v). After refluxing at 80° C. for 24 hour, the reaction mixture was significantly viscous, and no smells of unreacted monomers were detected.

The monomer components, molecular weight, glass transition temperature (Tg) and viscosity of the polymers are summarized in Table 4 below. Molecular weight of the TRIS-OH containing copolymers A-C was characterized by Gel Permeation Chromatography (GPC). The glass transition temperature (Tg) was characterized by rheometer. The adhesion and rheological properties of the polymers (tested by standard procedures) are summarized in Table 5 and Table 6, respectively (both below).

Example 3

Peel Force from Release Liner of PSA Formulated with Amines

Transdermal drug delivery systems comprising an amine drug and a polymer matrix comprising a silicone polymer may suffer from a peel force from release liner that increases overtime, eventually making it difficult to remove the release liner for use. Surprisingly, it was determined that a PSA as described herein that includes silicone moieties exhibits satisfactory peel properties over time when used in a transdermal drug delivery compositions formulated with an amine compounds, such as amine drugs.

To assess this property, copolymer C (MA/EHA/TRIS-Si/MEA/TRIS-OH) was formulated with three different amine compounds selected to be representative of primary, secondary and tertiary amine active agents, respectively, in the amounts set forth in the table below. The amine compounds used were phenethylamine ("PEA") (a primary amine), dioctylamine ("DOA") (a secondary amine), and trioctylamine ("TOA") (a tertiary amine). Peel force from a release liner (SCOTCHPAK®1022) was assessed as generally described in ASTM D3330/D3330-04 (Test Method A) after storage at ambient conditions (generally 20-25° C. and 30-70% relative humidity (RH)). In particular, samples are conditioned at 20-25° C. and 30-70% RH for at least 4 hours prior to testing, and room conditions are maintained at 20-25° C. and 30-70% RH during testing. Double-sided pressure-sensitive adhesive tape is applied to the sled of the adhesion/release tester (ChemInstruments AR-1000), and patch samples are applied to the double-sided pressure-sensitive adhesive tape. Peel force is assessed at a peel angle of 180; sample (strip) width of 0.5", and speed of 12 inches per minute. Results are set forth below reporting the average of three repeats for each sample:

| Formulation (w/w) | Peel Force From Release Liner (g/0.5", n = 3) | | | | |
|---|---|---|---|---|---|
| | T = 0 | T = 1 M | T = 2 M | T = 3 M | T = 4 M |
| Primary Amine | | | | | |
| 2.5% PEA + 97.5% Copolymer C | 11.9 | 16.9 | 16.0 | 24.3 | 25.7 |
| 5% PEA + 95% Copolymer C | 11.8 | 19.6 | 36.7 | 43.1 | 42.9 |
| Secondary Amine | | | | | |
| 2.5% DOA + 97.5% Copolymer C | 6.2 | 17.0 | 33.4 | 44.3 | 39.7 |
| 5% DOA + 95% Copolymer C | 8.3 | 25.4 | 32.0 | 36.3 | 34.9 |
| Tertiary Amine | | | | | |
| 2.5% TOA + 97.5% Copolymer C | 8.5 | 12.3 | 14.1 | 21.4 | 21.9 |
| 5% TOA + 95% Copolymer C | 8.2 | 10.9 | 11.4 | 15.4 | 18.6 |

As reflected in the table, the peel force from release liner increased over the first two months and then stabilized at an easy-to-peel level (20-45 g/0.5"). These results indicate that PSAs as described herein that include silicone moieties will exhibit satisfactory peel properties over time, even when formulated with amine drugs, such as when used in the polymer matrix of a drug-in-adhesive composition (as modeled above), or as a separate layer of a transdermal drug delivery composition comprising an amine drug.

TABLE 3

Exemplary PSAs.

| | Skin Mimicking Portion | | Optional Hydrophilic | Intermediate Portion | Hydrophobic Portion | | |
| --- | --- | --- | --- | --- | --- | --- | --- |
| Functions | TRIS-OH (Tg = 156° C.) Mimic skin lipid functional groups; Form H-bonds to skin (miscible in water) | GOEMA (Tg = ?) | Portion HEMA (Tg = 57° C.) Form H-bonds to skin; (miscible in water) | MEA (Tg = −50° C.) Block water penetration; Expose PSA's OH groups to skin; Protect H-bonds; (Immiscible in water) | TRIS-Si (Tg <0° C.) Block water penetration; Protect H-bonds (Immiscible in water) | EHA (Tg = −68° C.) | MA (Tg = 9° C.) |
| 1 | 5 | — | — | — | 70 | 5 | 20 |
| 2 | 10 | — | — | — | 65 | 5 | 20 |
| 3 | 10 | — | — | 30 | 35 | 5 | 20 |
| 4 | 5% | 5% | 10% | 70% | 10% | — | — |
| 5 | 7.5% | 7.5% | 15% | 80% | 10% | — | — |
| 6 | 10% | 10% | 20% | 90% | 10% | — | — |
| 7 | 5% | 5% | — | 60% | — | 20% | 10% |
| 8 | 7.5% | 7.5% | — | 50% | — | 20% | 15% |
| 9 | 10% | 10% | — | 40% | — | 20% | 20% |
| 10 | 10% | 10% | — | 60% | — | — | 20% |
| 11 | 7.5% | 7.5% | 5% | 65% | — | — | 15% |
| 12 | 5% | 5% | 10% | 70% | — | — | 10% |

TABLE 4

Properties of Copolymer A, B, and C.

| Copolymer | Chemical Structure (weight ratio) | Solid (w/w, %) | $T_g$ (° C.) | Mw (Dalton) | Viscosity (cP @ 23.5° C.) | Appearance | Solvents |
| --- | --- | --- | --- | --- | --- | --- | --- |
| A | MA/EHA/TRIS-Si/TRIS-OH = 20/5/70/5 | 57.1 | 3 | 103,753 | 776 | Colorless & Transparent | 2-Butanone/ Ethanol |
| B | MA/EHA/TRIS-Si/TRIS-OH = 20/5/65/10 | 58.6 | 10 | 125,602 | 961 | Colorless & Transparent | 2-Butanone/ Ethanol |
| C | MA/EHA/TRIS-Si/MEA/TRIS-OH = 20/5/35/30/10 | 53.9 | −8 | 109,396 | 749 | Colorless & Transparent | 2-Butanone/ Ethanol |

TABLE 5

Adhesion properties of Copolymers A, B, and C.

| Copolymer | Thumb Tack (1-10) | Probe Tack (g/0.5 cm$^2$) | 180° RL peel (g/0.5") | 90° SS peel (g/0.5") | Shear (min, 0.75", 250 g) |
| --- | --- | --- | --- | --- | --- |
| A | 5 | 50.5 | 4.5 | Del* | 334 |
| B | 3 | 0.5 | 4.0 | Del* | >5,000 |
| C | 8 | 186.7 | 20.4 | 113.2 | 111 |

Del*: delaminated from the backing.

TABLE 6

Rheological properties of Copolymers A, B, and C.

| | Copolymer A | | | | Copolymer B | | | | Copolymer C | | | |
| --- | --- | --- | --- | --- | --- | --- | --- | --- | --- | --- | --- | --- |
| ω (rad/s) | Eta* (P) | G' (dyn/cm$^2$) | G" (dyn/cm$^2$) | Tanδ | Eta* (P) | G' (dyn/cm$^2$) | G" (dyn/cm$^2$) | Tanδ | Eta* (P) | G' (dyn/cm$^2$) | G" (dyn/cm$^2$) | Tanδ |
| 0.01 | 1.1e$^6$ | 5.1e$^3$ | 9.6e$^3$ | 1.9 | 5.9e$^6$ | 4.5e$^4$ | 3.8e$^4$ | 0.8 | 7.3e$^5$ | 4.1e$^3$ | 6.0e$^3$ | 1.5 |
| 0.1 | 4.6e$^5$ | 2.8e$^4$ | 3.6e$^4$ | 1.3 | 1.8e$^6$ | 1.3e$^5$ | 1.3e$^5$ | 1.0 | 2.7e$^5$ | 1.9e$^4$ | 1.9e$^4$ | 1.0 |
| 1 | 1.7e$^5$ | 1.0e$^5$ | 1.3e$^5$ | 1.3 | 6.4e$^5$ | 3.9e$^5$ | 5.1e$^5$ | 1.3 | 8.1e$^4$ | 5.8e$^4$ | 5.7e$^4$ | 1.0 |
| 10 | 6.6e$^4$ | 3.6e$^5$ | 5.6e$^5$ | 1.6 | 2.7e$^5$ | 1.4e$^6$ | 2.3e$^6$ | 1.6 | 2.6e$^4$ | 1.8e$^5$ | 1.9e$^5$ | 1.1 |
| 100 | 3.0e$^4$ | 1.4e$^6$ | 2.7e$^6$ | 1.9 | 1.3e$^5$ | 6.2e$^6$ | 1.1e$^7$ | 1.8 | 9.2e$^3$ | 5.7e$^5$ | 7.2e$^5$ | 1.3 |

What is claimed is:

1. A transdermal drug delivery composition comprising an amine drug and a pressure-sensitive adhesive polymer (PSA), wherein the PSA has a three-part structure comprising:

(i) a skin-mimicking portion polymerized from monomers including skin-mimicking monomers having a skin-mimicking polar group, wherein the skin-mimicking monomers are selected from monomers having a glucosyl group, monomers having two or more hydroxyl groups, and combinations of any two or more thereof,
(ii) a weakly hydrophilic portion polymerized from monomers including weakly hydrophilic monomers, and
(iii) a hydrophobic portion polymerized from monomers including hydrophobic monomers, wherein the skin-mimicking portion is located at a skin-contacting region of the composition, and the weakly hydrophilic portion is located between the skin-mimicking portion and the hydrophobic portion.

2. The transdermal drug delivery composition of claim 1, wherein the skin-mimicking monomers are selected from the group consisting of glycosyloxyethyl methacrylate (GOEMA), N-[Tris(hydroxylmethyl)methyl]acrylamide (TRIS-OH), 2,3-dihydroxylpropyl acrylate, glycerol monomethacrylate, 1,1,1-trimethylolpropane monoallyl ether, pentaerythritol mono-acrylate, pentaerythritol mono-methacrylate, sorbitol mono-acrylate, sorbitol mono-methacrylate, and acrylates containing one or more catechol groups, and combinations of any two or more thereof.

3. The transdermal drug delivery composition of claim 1, wherein the weakly hydrophilic monomers are selected from the group consisting of methoxy ethylacrylate (MEA), polyethylene glycol mono-methacrylate (PEGMA), and combinations thereof.

4. The transdermal drug delivery composition of claim 1, wherein the hydrophobic monomers are selected from the group consisting of vinyl acetate (VA), methyl methacrylate (MMA), methyl acrylate (MA), n-butyl acrylate (n-BA), 2-ethylhexyl acrylate (2-EHA), tris(trimethylsilyloxy)silyl) propyl methacrylate (TRIS-Si), and combinations of any two or more thereof.

5. The transdermal drug delivery composition of claim 1, wherein the PSA is polymerized from further monomers selected from the group consisting of hydrophilic hydroxyethyl methacrylate (HEMA), hydroxyethyl acrylate (HEA), acrylic acid (AA), methyl acrylic acid (MAA), and combinations of any two or more thereof.

6. The transdermal drug delivery composition of claim 1, wherein the skin-mimicking portion is polymerized from TRIS-OH monomers, the weakly hydrophilic portion is polymerized from MEA monomers, and the hydrophobic portion is polymerized from MA, EHA and TRIS-Si monomers.

7. The transdermal drug delivery composition according to claim 1, wherein the amine drug is comprised in a drug-in-adhesive matrix comprising the PSA.

8. The transdermal drug delivery composition according to claim 1, wherein the PSA is comprised in a non-drug containing layer.

9. A transdermal drug delivery composition according to claim 1, further comprising a backing layer.

10. A transdermal drug delivery composition according to claim 1, further comprising a release liner.

11. A transdermal drug delivery composition according to claim 10, wherein the composition exhibits a peel force from the release liner of 20-45 g/0.5" after storage for three months at ambient conditions.

12. A transdermal drug delivery composition according to claim 10, wherein the composition exhibits a peel force from the release liner of 20-45 g/0.5" after storage for four months at ambient conditions.

13. A transdermal drug delivery composition according to claim 1, wherein the amine drug is one or more selected from the group consisting of amphetamine, methylphenidate, rivastigmine, rotigotine, fentanyl, paroxetine clonidine, amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, flavoxate, homatropine, imipramine, loxapine, mazaticol, metixene, oxybutinin, oxyphencyclimine, phenglutarimide, physostigmine, piperidolate, pirenzepine, procyclidine, profenamine, propiverine, scopolamine, telenzepine, theophylline, tolterodine, trimipramine, trihexyphenidyl, tropatepine, and tropicamide.

14. A method of making a transdermal drug delivery composition according to claim 7, comprising blending the PSA with an amine drug.

15. A method of making a transdermal drug delivery composition according to claim 8, comprising forming a transdermal drug delivery composition comprising a non-drug containing layer comprising the PSA and a polymer matrix layer comprising the amine drug.

16. A method of transdermally delivering an amine active agent, comprising applying a composition according to claim 1 to the skin of a subject in need thereof.

17. The method of claim 16, wherein the composition remains adhered to the skin upon exposure to water.

* * * * *